United States Patent [19]
Lagerway et al.

[11] Patent Number: 6,142,934
[45] Date of Patent: Nov. 7, 2000

[54] OBJECTIVE LENS SYSTEM FOR IMAGING INSTRUMENT

[75] Inventors: William H. Lagerway, Auiburn; David G. Perkins, Syracuse; William M. Wrisley, North Syracuse; Ronald A. Hauptli, Warners, all of N.Y.

[73] Assignee: Welch Allyn, Inc., Skaneateles Falls, N.Y.

[21] Appl. No.: 09/221,922

[22] Filed: Dec. 28, 1998

Related U.S. Application Data

[63] Continuation-in-part of application No. 09/052,570, Mar. 31, 1998.
[60] Provisional application No. 60/043,374, Apr. 4, 1997, and provisional application No. 60/075,406, Feb. 20, 1998.

[51] Int. Cl.[7] .................................................. A61B 1/227
[52] U.S. Cl. ........................ 600/200; 600/156; 600/167
[58] Field of Search ................................. 600/172, 176, 600/109, 200, 167; 385/119

[56] References Cited

U.S. PATENT DOCUMENTS

| | | | |
|---|---|---|---|
| 4,111,529 | 9/1978 | Yamashita | 600/176 |
| 4,380,998 | 4/1983 | Kieffer et al. | |
| 4,777,524 | 10/1988 | Nakajima et al. | 600/167 |
| 4,895,138 | 1/1990 | Yabe | 600/172 |
| 4,947,245 | 8/1990 | Ogawa . | |
| 5,239,984 | 8/1993 | Cane . | |
| 5,363,839 | 11/1994 | Lankford . | |
| 5,658,235 | 8/1997 | Priest . | |
| 5,733,029 | 3/1998 | Monroe | 600/200 |
| 5,777,797 | 7/1998 | Miyano | 600/176 |
| 5,891,015 | 4/1999 | Strähle | 600/167 |
| 5,902,232 | 5/1999 | Igarashi | 600/167 |

*Primary Examiner*—John P. Leubecker
*Attorney, Agent, or Firm*—Wall Marjama & Bilinski

[57] ABSTRACT

A retrofocus objective lens system which is conducive for an otoscope includes a first group of optical elements positioned at a distal portion and a second group of optical elements proximally spaced from the first group of optical elements. The first group of optical elements includes at least one negative small diameter lens while the second group of optical elements include a plurality of small diameter lenses having an aggregate optical power which is positive, allowing an image of interest to be transmitted through the system without any intermediate imaging planes, and without the need for rod lenses. The first and second lens groups are retained in a plurality of linearly interconnected lens tubes such that one lens tubes is linearly adjustable in relation to the remaining lens tubes in order to vary the focal length of the lens system.

20 Claims, 6 Drawing Sheets

OBJECTIVE LENS SYSTEM FOR IMAGING INSTRUMENT

CROSS REFERENCE TO RELATED APPLICATIONS

This application is a continuation-in-part of U.S. Ser. No. 09/052,570, filed Mar. 31, 1998, which is based upon provisional applications U.S. Ser. No. 60/043,374, filed Apr. 4, 1997, and U.S. Ser. No. 60/075,406, filed Feb. 20, 1998.

FIELD OF THE INVENTION

This invention relates to the field of imaging instruments, and particularly to a retrofocus objective lens system for use in an imaging instrument such as an otoscope.

BACKGROUND OF THE INVENTION

An otoscope is a portable, direct viewing examination instrument that aids in the observance and study of the inner ear canal, including the tympanic membrane. Many otoscopes are presently known, each typically having a housing including a frusto-conical head portion and specula capable of being placed a predetermined distance within the ear canal of a patient. The interior of the housing includes an optical viewing system, as well as an illumination system for providing light in a coaxial manner with the viewing system. In use, the optics permit viewing using an eyepiece attached to a proximal end of the housing.

With the advent of "telemedicine", videoized versions of medical examination instruments, including otoscopes, have been developed, such as those described in U.S. Pat. No. 5,363,829 issued to Lankford; U.S. Pat. No. 5,239,984, issued to Cane, et al; and U.S. Pat. No. 4,947,245, issued to Ogawa, et al. In each of the above, a miniature video camera, such as a CCD or other electronic sensor, is positioned either within the interior of the instrument or adjacently coupled thereto. The electronic sensor includes a light receiving surface or substrate which receives a focused optical image of a target of interest through the optical viewing system. The sensor then converts the optical signal into an electrical signal and subsequently through processing electronics into a monitor-ready video signal.

In order to provide a complete ear examination of a patient, it is desirable that the otoscope include the capability of producing a stream of air for stimulating the tympanic membrane. This feature is known as insufflation.

To provide insufflation capability, the inner tip housing of the otoscope must be sufficiently large enough to accommodate the illumination system, the optical viewing system, and an air path permitting insufflation.

In addition, and though the ear canal is a relatively small chamber, it is also desirable to provide a sufficient field of view to allow the entirety of the tympanic membrane (approximately 8 mm) to be viewed at one time during an examination. In the past, videoized versions of otoscopes have utilized relay lens systems to achieve this goal.

Several attempts to attach a video camera to a standard otoscope have proved less than successful due to compromises in field size, vignetting (clipping) and lack of video lens interchangeability. In addition, the lens elements must be under three millimeters in diameter in order to fit inside the specula tip of the otoscope.

In order to achieve the relatively long total conjugate length (approximately 99 mm) of a video otoscope, While maintaining the small element diameters (under 3 mm) required, the resulting optical system tends to be complex. Most of these lens systems 126 are composed of some form of objective means in the distal portion 122 of the otoscope, followed by one or more relay configurations. This type of system has many disadvantages based upon to its overall complexity, therefore producing greater likelihood of manufacturing errors, and requiring a plurality of intermediate imaging planes 138, as shown in FIG. 1. The intermediate image planes 138 are necessitated by the relay configurations and are subject to cosmetic issues.

As shown in FIG. 1, these known lens systems include a number of axially disposed optical elements which transmit the optical signal through a series of intermediate image planes located between the target plane 140 and the image substrate 134 of a miniature video camera along an axis 130.

For a normally constructed objective lens system, the object and image plane conjugates are essentially in proportion to the system magnification, or more specifically to the ratio of M and 1/M, in which M is the system magnification. By knowing the desired magnification, (1:1), (1:2), etc., it is straight forward to calculate the total conjugate length (the distance from the object to image) for any focal length. Similarly, the focal length required to achieve a desired total conjugate length is also easily calculated.

It is readily known that an objective lens system operating at unit magnification (1:1) is normally located equidistant from the object and image planes. For an objective lens system to operate at a reduction of 0.5 (1:2), the object conjugate must normally be twice that of the image conjugate.

Most often undesirable or unattainable objective positions are produced with the lens systems typically employed in many videoized instruments, including otoscopes. It is desirable to produce a system that allows for the placement of the objective lens at a more favorable location.

SUMMARY OF THE INVENTION

Therefore, it is an object of the present invention to provide a viewing system for an imaging instrument which overcomes the disadvantages of the prior art.

It is another primary object of the present invention to provide an imaging instrument having an optical viewing system that does not include any intermediate imaging planes.

Another object of the invention is to provide an optical system for a diagnostic instrument such as an otoscope which provides adequate spacing to allow viewing while still allowing permitting incorporation of insufflation or other features.

It is yet another object of the invention to provide an improved objective lens system for an imaging instrument, particularly an instrument requiring small diameter lenses.

Therefore, and according to a preferred aspect of the present invention, there is provided a retrofocus objective lens system for an imaging instrument, comprising;

a first group of optical elements positioned at a distal portion of said system;

a second group of optical elements proximally spaced from said first optical element and aligned along an optical axis; and a single imaging plane disposed along said optical axis proximal to said first optical element and said plurality of intermediate optical elements, wherein said first group of optical elements includes at least one lens component, said at least one lens component having negative optical power, and said second group of optical elements including a plurality of elements having an aggregate optical power which is positive and wherein an image of a target viewed by said system is focused only at the imaging plane.

Preferably, the first group of optical elements is defined by a single small diameter negative lens, the diameter in fact being smaller than its corresponding focal length. The second group of optical elements includes a combination of positive and negative lens having an overall or aggregate positive optical power which allows an image transferred through the system to be focused only at the single image plane, preferably onto the imaging substrate of a suitably positioned electronic sensor.

According to a preferred embodiment, the second group of optical elements includes a plurality of lenses including respective second, third, and fourth lens components. Preferably, the second lens and fourth lenses are positive, and the third lens is a doublet containing a negative lens contiguous with a positive lens and having an overall or aggregate optical power which is negative. An aperture stop of convenient size is suitably positioned between the first and second lenses according to this design.

In an alternative embodiment, the second optical group includes a second positive lens, a third lens proximally spaced relative to the second lens, a fourth lens proximally spaced relative to the third lens, and a fifth lens proximally spaced relative to the fourth lens. In this system design, the second and fifth lenses are positive, and the fourth lens element is a doublet containing a negative lens contiguous with a positive lens such that the aggregate optical power of the doublet is negative. The aperture stop, according to this system design, is positioned between the second and third lenses.

According to another preferred aspect of the present invention, there is provided an otoscope having a retrofocus objective lens system for reducing an object onto a single image plane, said lens system comprising:

a first group of optical elements positioned at a distal portion of said system;

a second group of optical elements proximally spaced from said first group of optical elements and aligned along an optical axis;

a single imaging plane disposed proximally from said second group wherein an image of a target of interest is transmitted through said system without intermediate imaging planes.

In a preferred embodiment, each group of optical elements is disposed in a lens tube or cell retained within an instrument housing. More preferably, the elements used in the objective lens system are sized such that coaxial illumination and insufflation features can be included in an otoscope without interfering with the viewing of an object through the objective lens system.

According to yet another embodiment there is described an otoscope comprising a housing including a distal tip opening, an imaging element disposed in relation to a proximal end of said housing; and an optical system disposed within said housing and aligned between said distal tip opening and said imaging element, wherein said optical system contains focussing means for focussing an optical image of a target of interest at said imaging element without any intermediate imaging planes between said target and said imaging element. Preferably, the otoscope includes illumination means for illuminating the target of interest through the distal tip opening and insufflation means for stimulating the tympanic membrane, each being disposed in the housing without interfering with the functions of the optical system.

An advantageous feature of the present invention is that a retrofocus lens system, as described, produces desirable objective positions and includes a long overall length using small diameter lens elements, yet produces minimal distortion and minimal vignetting, making this system ideal for an imaging instrument such as an otoscope.

A further advantage is that the above optical system can be suitably arranged in an instrument housing of compact size without compromising the ability to provide other needed instrument features, such as insufflation in the case of an otoscope.

These and other objects, advantages, and features will be described in the following Detailed Description of the Invention which should be read in conjunction with the accompanying drawings.

DETAILED DESCRIPTION OF THE INVENTION

The following discussion describes an optical viewing system according to a specific embodiment for use with a specific medical examination instrument, i.e.: an otoscope. As will be apparent from the following discussion, however, there are other suitable applications for an optical viewing system embodying the concepts described herein. That is, the described objective lens system can be used in other medical (endoscopic) and/or non-medical (such as borescopic) applications involving the examination of cavities having narrow or shaped openings.

Figure 1:
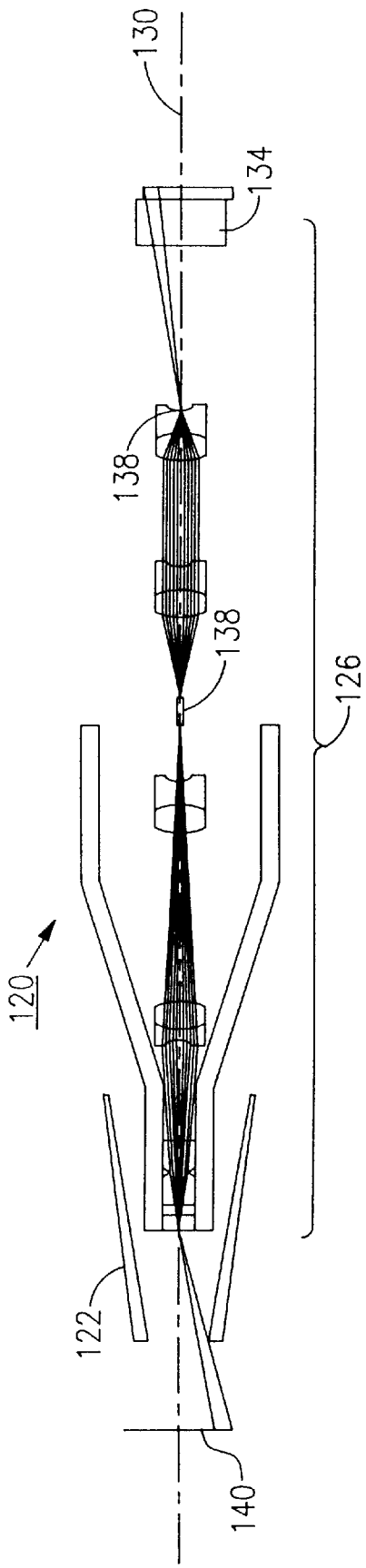
FIG. 1 is a partial sectional view of an otoscope having an optical viewing system according to the prior art, including a partial ray trace of a target object as transmitted through the system.
Figure 2:
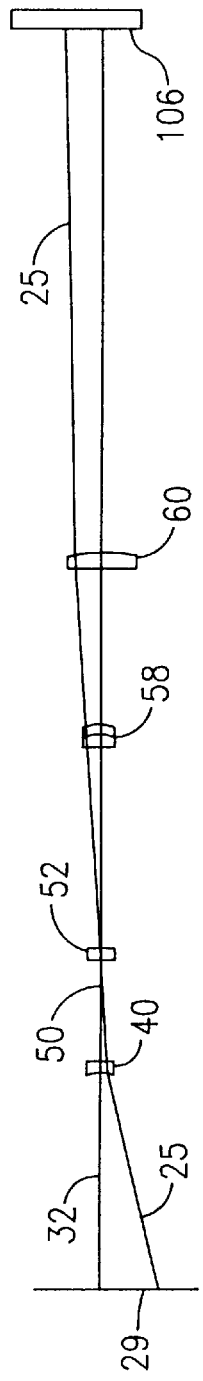
FIG. 2 is a diagrammatic view of an optical viewing system in accordance with a preferred embodiment of the present invention illustrating the transmission of a chief ray relative to the optical axis of the system.
Figure 3:
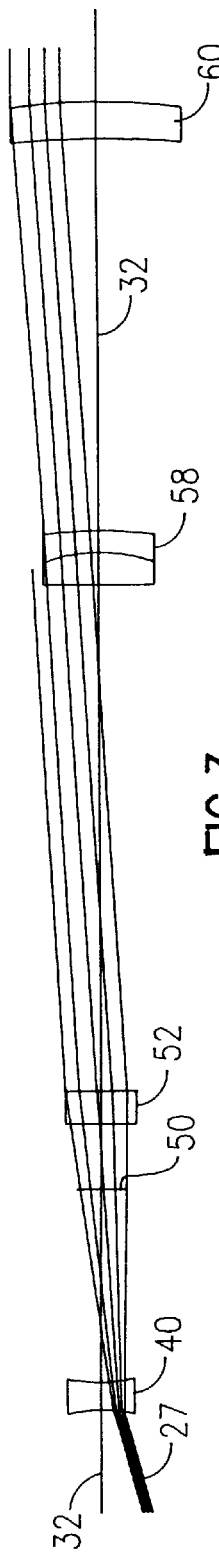
FIG. 3 is the ray trace diagram of FIG. 2, illustrating a bundle of rays through the optical viewing system relative to the optical axis.

Reference is now made to FIGS. 2–6 which relates to an optical viewing system 12 in accordance with the present invention. Referring first to FIGS. 2 and 3, the viewing system 12 is shown diagrammatically. A first lens 40 is disposed at the distal end of the system 12. A key feature of the present invention is that the first lens 40 is a negative lens of suitable power which is aligned along a system viewing axis 32. An aperture stop 50 is disposed proximally from the first lens 40 and is aligned therewith along the viewing axis 104. A second lens 52 is disposed somewhat adjacently and proximally from the aperture stop 50. According to the present embodiment, the second lens 52 is a positive lens. A third lens 58 in the form of a doublet is disposed proximally from the previously described elements 40, 52 at a predetermined distance followed by a fourth positive lens 60, each also aligned with the viewing axis 32.

As shown in FIGS. 2 and 3, a chief ray 25, FIG. 2 or bundle of rays 27, FIG. 3, entering the system from a target plane 29 are first directed through the negative lens 40 which diverges the light and fills the aperture stop 50. Light emerging the aperture stop 50 passes through the second lens 52 having sufficient power to partially converge the light which then passes to the doublet 58 having an aggregate negative power which further diverges the light transmitted to the fourth positive lens 60 which essentially collimates the light until the light is focused at the imager 106. There are no intermediate imaging planes. In use, an optical signal is channeled through each of the above disposed optical elements and is ultimately focused at the imaging substrate of the imager 106.

Figure 4:
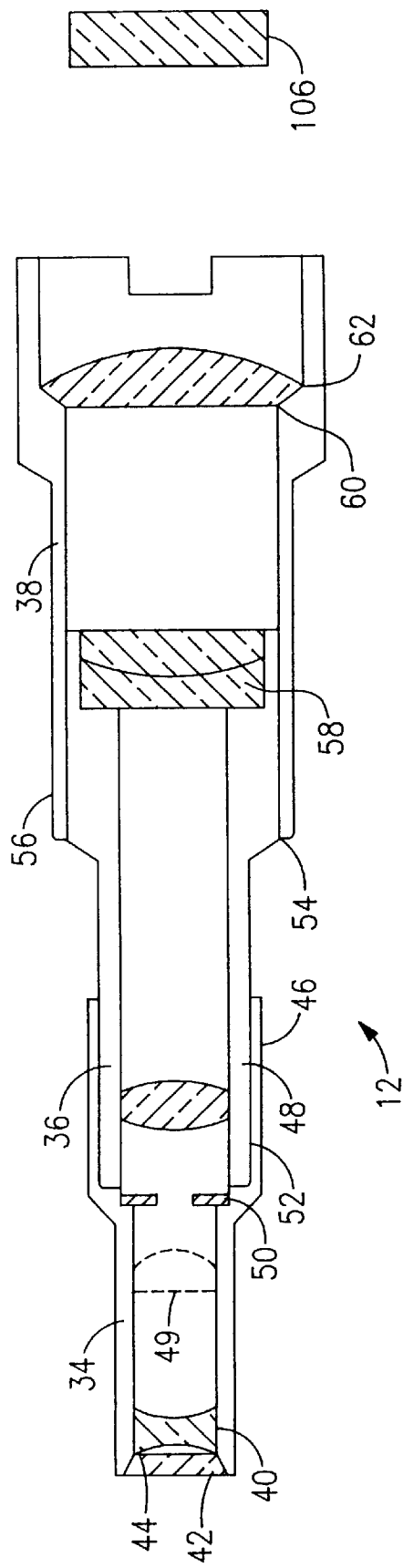
FIG. 4 is a sectional view of the optical viewing system of FIGS. 2 and 3 as contained within a lens cell in accordance with a preferred embodiment of the invention.
Figure 5:
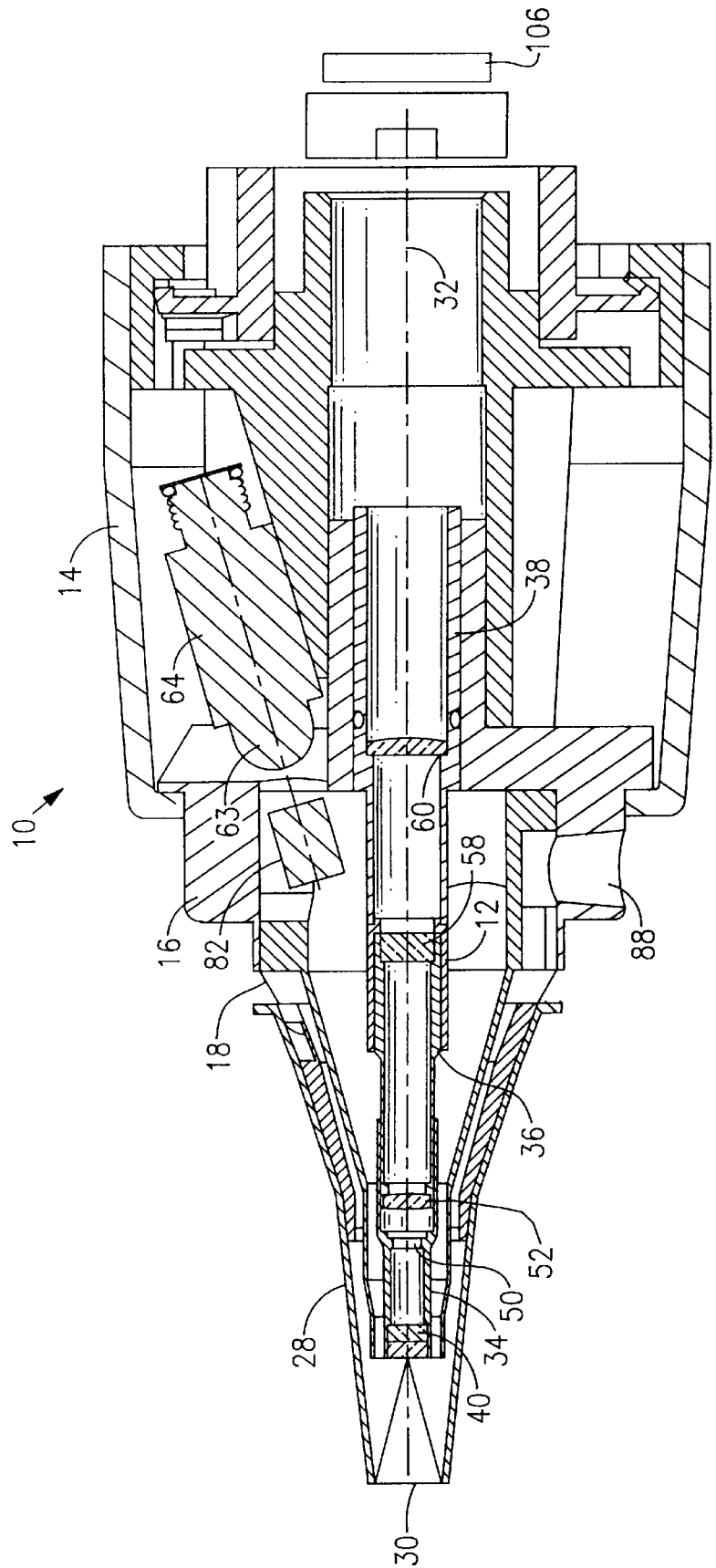
FIG. 5 is an enlarged partial sectional view of an otoscope having the contained optical viewing system of FIG. 4.
Figure 6:
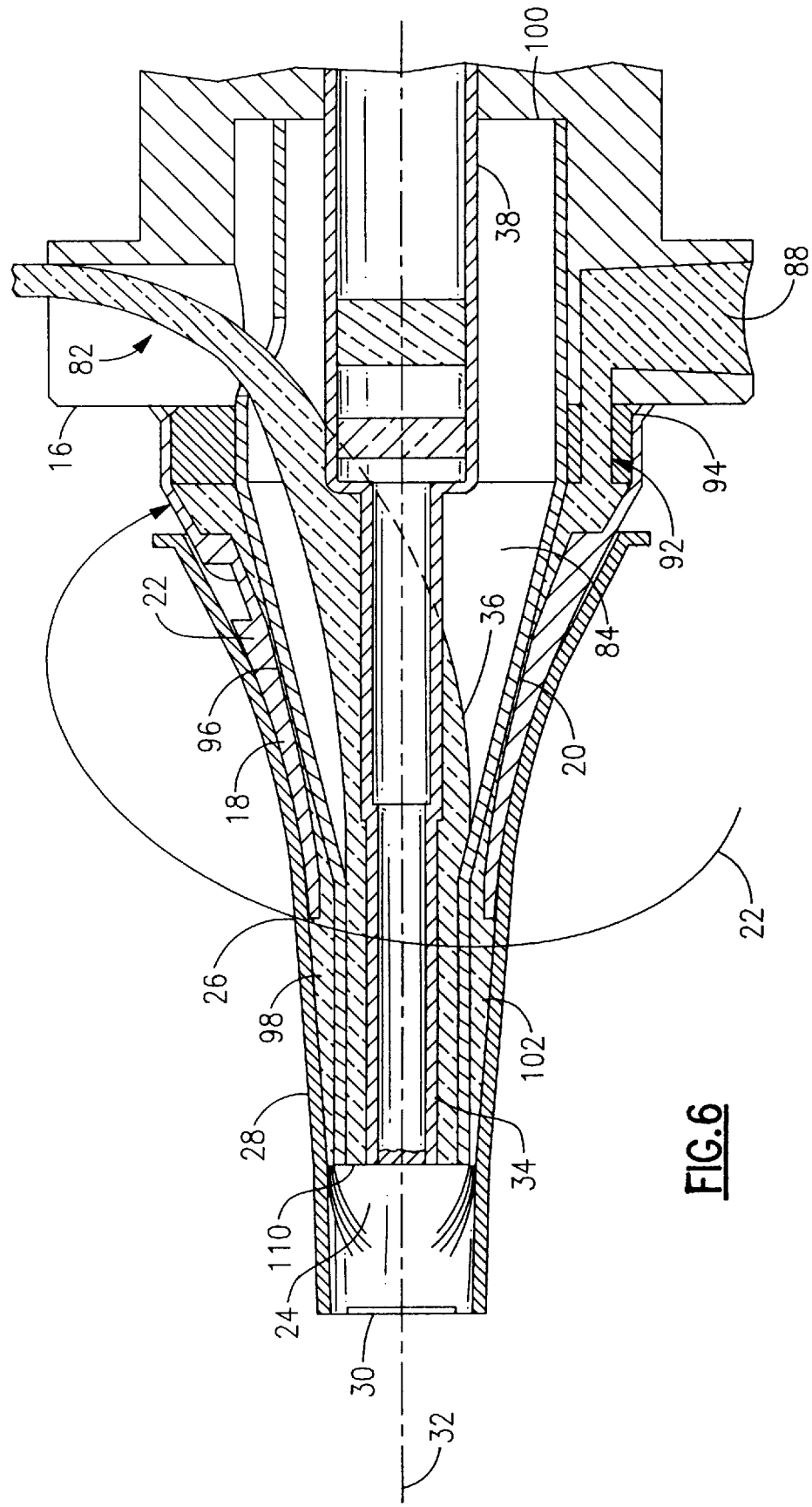
FIG. 6 is a sectional view of FIG. 5, further indicating the combination of insufflation and illumination with the optical viewing system of FIGS. 2–5.
Figure 7:
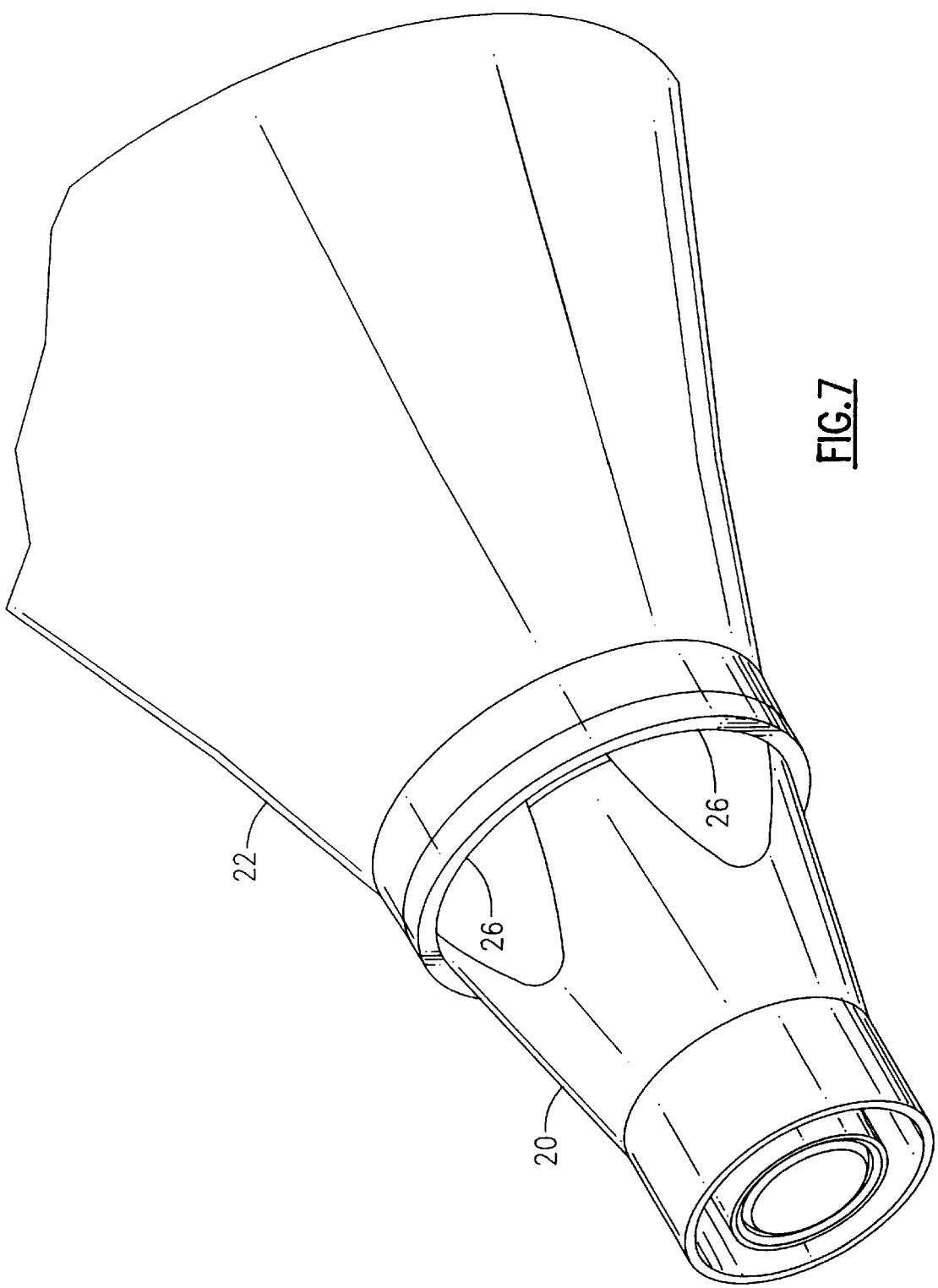
FIG. 7 is a partial front perspective view of an otoscopic head including a modified insufflation feature.

Referring to FIGS. 4–6, the objective system 12 of the invention is shown in use within an otoscopic instrument head 10. Referring to FIG. 5, the illustrated otoscopic instrument head 10 includes a substantially cylindrically shaped proximal housing portion 14, an intermediate housing portion 16, and a frusto-conical distal insertion portion 18. The distal insertion portion 18 has a defined interior which includes overlapping and conically shaped inner and outer tip housings 20, 22, each tip housing having a respective distal tip opening 24, 26 coaxially arranged along a defined optical axis 32. The inner tip housing 20 extends distally from the tip opening 26 of the outer tip housing 22. A hollow safety speculum 28, preferably made from a plastic material and having a distal tip opening 30, is mounted onto the conical periphery of the distal insertion portion 18, also in overlapping relation. Each of the distal tip openings 24, 26, 30 are coaxial with one another along the optical axis 32, the tip openings of the mounted speculum 28 and the distal insertion portion 18 being slightly displaced from the tip opening 24 of the inner tip housing 20.

An illumination assembly 63 includes a miniature halogen lamp 64 which is disposed within the proximal housing portion 14. Light from the halogen lamp 64 is directed to one end of a bundle of optical fibers 82 (partially shown), the fibers being fanned out into a first annular space 84 formed between the exterior portion of a series of interconnected lens tubes 34, 36, 38 supporting the viewing system 12 and the interior wall of the inner tip housing 20 so as not to interfere with the transmission of optical data through the lens tubes. The bundle of fibers 82 terminate at the distal tip opening 24 of the inner tip housing 20, preferably as a polished light emitting end 110 which is coterminous with a first lens tube 34, as described below.

Figure 8:
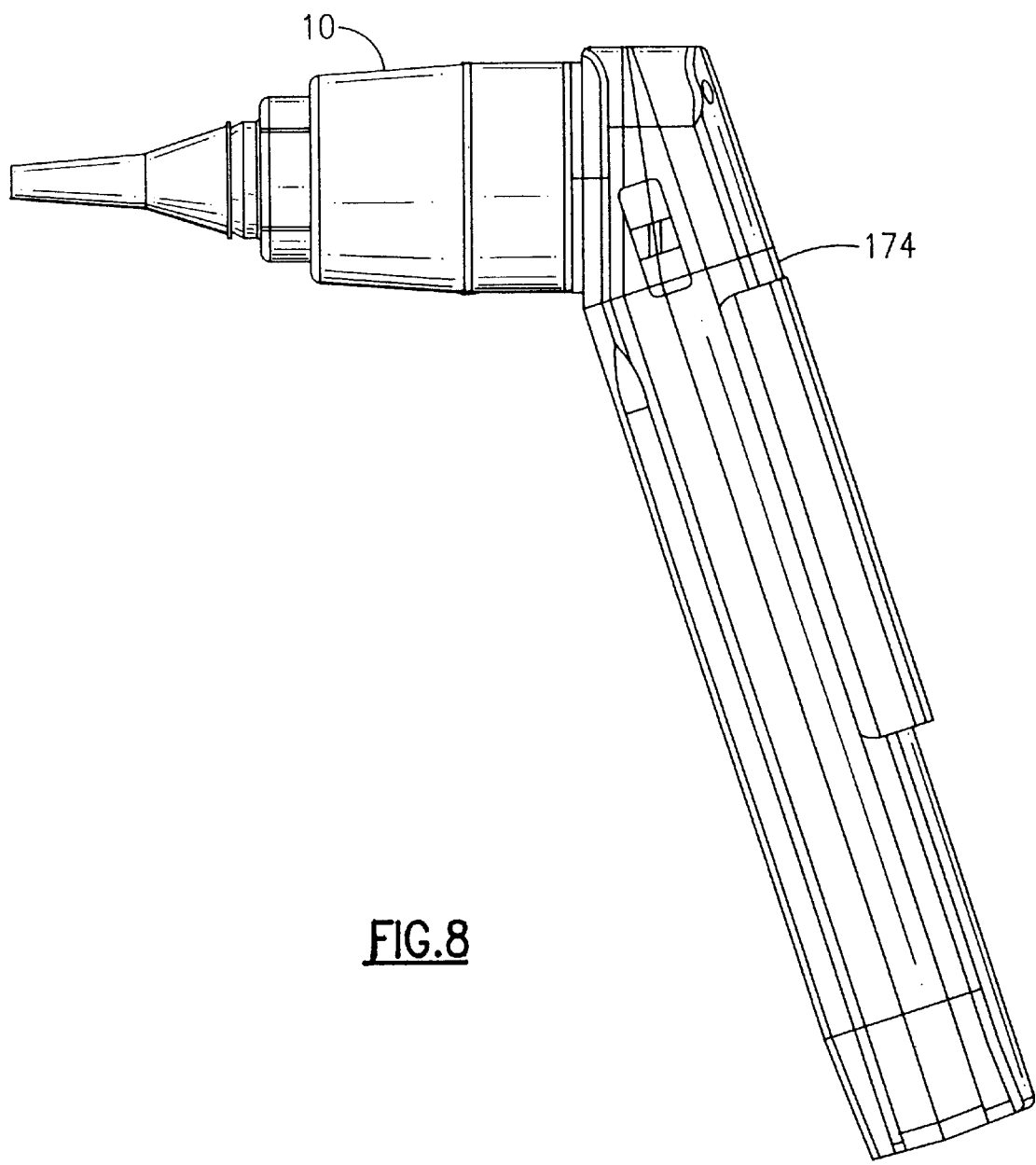
FIG. 8 is a side partial view of a compact otoscopic head having the optical system of FIGS. 2–6 as used in combination with a hand-held multimedia instrument.

As noted, the safety speculum 28 is releasably attached to the exterior of the front insertion portion 18. A preferred attaching arrangement is described in commonly owned U.S. Pat. No. 4,380,998 issued to Kieffer, et al, the entire contents of which are herein incorporated by reference. The instrument head 10 is locked into engagement with the front interface 170 of the instrument, as shown in FIG. 8.

As noted above, the above lens system 12 is disposed within the series of interconnected lens tubes 34, 36, 38, each coaxially arranged within the interior of the instrument head 10 along an optical axis 32. The first lens 40 is disposed in a first lens tube 34 adjacent the distal opening 24 of the inner tip housing 20 along with a plano glass section 42, preferably disposed directly in front of the first lens 40.

Preferably, the interior wall of the first lens tube 34 defines a shoulder 44 for supporting and positioning the adjacent elements 40, 42. The proximal end 46 of the first lens tube 34 is wider than that of the remainder of the tube and is sized for receiving the distal end 48 of an attached second lens tube 36. The aperture stop 50 and the second lens 52 are each retained within the widened proximal end 46 of the first lens tube 34 prior to the distal end 48 of the second lens tube 36. The aperture stop 50 provides the proper direction of the image through the objective, limits the distortion of the image, and limits vignetting at the full field position. The second lens 52 is a positive lens of sufficient power. A proximal end of the second lens tube 36 is retained within a cavity 54 of the distal end 56 of a third lens tube 38, wherein a third lens 58 is attached at the proximal end of the second lens tube 36. According to this embodiment, the third lens 58 is a doublet containing respective concave and convex lenses of an appropriate size. The third lens 58, preferably having an overall or aggregate negative optical power provides a large dispersion and is used to provide color correction to the image.

Finally, and according to this particular system design, the fourth lens 60 is provided and disposed in a cavity 62 at approximately the midpoint of the length of the third lens tube 38. As noted above, the fourth lens 60 is preferably of positive optical power and functionally takes collimated parallel light arriving from the third lens 58 and focuses the light down to the imager 106, providing for correction of the direction of the image.

It should be readily evident that the fourth lens 60 could alternately be disposed within a pilot section (not shown) of the instrument 174.

As should be apparent from the design of the above system, there are no intermedia image planes thereby defining a retrofocus objective lens system. The lens system has an overall fixed length, a fixed focal length, and a fixed magnification.

The defining characteristics of the lens system, such as the focal length, are adjustable by changing the position of the first lens tube 34 in relation to the second lens tube 36.

Specifics for the design of the above system 12 are provided in Table I and the parameters of the lens elements are provided in Table II.

TABLE I

| | |
|---|---|
| Overall length of lens system (TCL) | 82.78 mm |
| Focal Length of lens system (EFL) | 10.076 mm |
| Back focal length of lens system (BFL) | 36.432 mm |
| Lens diameters (distal end) | less than 3 mm |
| Total conjugate distance (distance from target plane to image plane) | 98.78 mm |
| Distortion | less than 5% |
| Vignetting (at full field position) | less than 20% |
| Magnification | 0.5 |
| Field of view | 8.3 mm |
| Target distance | 16 mm |

TABLE II

| Optical Element | Radius | Material | Thickness |
|---|---|---|---|
| Plano Glass | Plano | BK7 | 1.0000 |
| First Lens Element | −3.101 3.101 Concave | BK7 | 0.7500 |

TABLE II-continued

| Optical Element | Radius | Material | Thickness |
| --- | --- | --- | --- |
| Second Lens Element | 19.7350 | BK7 | 1.0000 |
| | −7.226 Convex | | |
| Third Lens Element Doublet | −8.7590 Concave | BK7 | 1.0000 |
| | −2.9700 | F2 | 0.7500 |
| | −7.4700 Convex | | |
| Fourth Lens Element | −13.332 Concave | BK7 | 1.0000 |
| | −8.3670 Convex | | |

The aperture stop 50 limits the distortion to under 5% and vignetting to under 20% at the full field position. The lens system achieves a magnification of 0.5 reduction for an object having a diameter (field of view) of 8.3 mm and positioned at an object or target distance of 16 mm from the piano glass section 42.

It should be readily apparent to one of sufficient skill in the field that it is possible to vary the position of at least some of the lens elements or alternately add lens elements to the above retrofocus objective lens system design and achieve the desired results.

For example, and as shown in phantom in FIG. 4, a fifth lens 49 can be added to the above system and positioned between the first lens 40 and the aperture stop 50 in the first lens tube 34. Moreover, it is also possible to selectively vary the position of certain elements in the described system depending on the optical distance. For example, by adjusting the separation between lenses 40 and 52, by up to approximately 0.35 mm, the optical working distance can be varied from 16 mm to infinity.

Referring to FIG. 6, an insufflation port 88 is provided in the intermediate housing portion 16, the port being adequately sized to receive a fitting (not shown). The insufflation port 88 defines one end of a passageway extending into the interior of the distal insertion portion 18. The fitting allows a known depressible pneumatic bulb (not shown) to be connected thereto for directing air (or creating a vacuum) through the path 92 which is defined through an opening of an interior wall 94 into a second annular space 96 between the inner and outer tip housings 20, 22. The air passes through the annular space and exits the distal tip opening 26 of the outer tip housing 22 into a third annular space 98 defined between the inner tip housing 20 and the interior of the safety speculum 28. The directed air exits through the distal tip opening 30 of the safety speculum 28. A rear wall 100 according to this embodiment acts to seal the assembly, to prevent air from passing through the rear portion of the instrument head, while the mounted safety speculum 28 assists in preventing air leakage other than through the distal tip opening 30.

In use, the target of interest (e.g., the interior of the ear canal) is viewed by the instrument by placing the front insertion portion 18 into an ear canal (not shown) of interest, placing the tympanic membrane (not shown) approximately 16 mm away from the negative lens 40. The retrofocus objective lens assembly 12 through the aligned tip opening 30, 24 projects an optical image of the target (approximately 8 mm in size) along the optical viewing axis 32, FIG. 2, ultimately focusing the image onto the imager 106, FIG. 2.

Insufflation can be further achieved in the manner shown in FIG. 8, wherein the outer tip housing 22 includes a predetermined number of flattened areas 80 provided on the outer periphery thereof. Other variations can easily be imagined.

PARTS LIST FOR FIGS. 1–8

10 instrument head
12 objective lens system
14 housing portion
18 insertion portion
20 inner tip housing
22 outer tip housing
24 tip opening
25 chief ray
26 tip opening
27 bundle of rays
28 speculum
29 target plane
30 distal tip opening
32 optical axis
34 first lens tube
36 second lens tube
38 third lens tube
40 first lens
42 plano glass section
44 shoulder
46 proximal end
48 distal end
50 aperture stop
52 second lens
54 cavity
56 distal end
58 third lens
60 fourth lens
62 cavity
63 illumination assembly
64 halogen lamp
80 flattened areas
82 optical fiber bundle
84 first annular space
88 insufflation port
92 path
94 interior wall
96 annular space
98 third annular space
100 rear wall
106 imager
110 polished end
122 distal portion
126 viewing system
130 axis
134 image substrate
138 intermediate imaging planes
140 target plane
170 front interface While the foregoing description and drawings represent the preferred embodiments of the present invention, it will be understood that various changes and modifications may be made without departing from the spirit and scope of the present invention.

We claim:

1. An otological imaging instrument for viewing an ear interior, said instrument comprising:

an instrument housing including a frusto-conical insertion portion at a distal end thereof;

an electronic imager disposed in a proximal end of said instrument housing opposite said distal end;

illumination means disposed within said insertion portion for illuminating the interior of the ear for viewing; and a retrofocusing lens system for reducing an object onto said proximally disposed imager at a single imaging plane located at said proximally disposed imager without the need of intermediate imaging planes and rod lenses, said retrofocusing lens system including a plurality of optical elements housed within a plurality of linearly interconnected lens tubes retained within said instrument housing, at least one of said lens tubes being linearly adjustable in relation to the remaining lens tubes in order to vary the focal length of the lens system, said plurality of optical elements including a first group of optical elements positioned within the frusto-conical insertion portion of said instrument housing opposite from said proximal end and a second group of optical elements disposed proximally from said first group, said first and second groups being aligned along an optical axis and in which said first group includes at least one first negative lens and said second group includes a plurality of lenses having an aggregate positive optical power.

2. The instrument as recited in claim 1, wherein said illumination means includes a plurality of optical fibers having distal light-emitting ends which are substantially coterminous with said first group of optical elements.

3. The instrument as recited in claim 2, wherein at least one lens tube and an interior wall of said insertion portion define a first annular space.

4. The instrument as recited in claim 3, wherein said plurality of optical fibers extends through said first annular space.

5. The instrument as recited in claim 1, wherein said second group of optical elements includes a second lens, a third lens spaced proximally relative to said second lens, and a fourth lens spaced proximally relative to said third lens, each of said second and said fourth lenses being positive lenses.

6. The instrument as recited in claim 5, wherein said third lens is a doublet containing a negative lens contiguous with a positive lens, said doublet having a negative aggregate optical power.

7. The instrument as recited in claim 1, wherein said first group of optical elements is retained within a first lens tube of said interconnected lens tubes.

8. The instrument as recited in claim 7, wherein said first lens tube is linearly adjustable relative to an adjacent second lens tube so as to adjust the relative focal length of said retrofocusing lens system.

9. The instrument as recited in claim 8, wherein said first lens tube includes a widened proximal end which is sized to receive a distal end of said second lens tube in overlapping engagement therewith and allowing relative linear adjustment of each of said first and second lens tubes so as to adjust the relative focal length of said retrofocusing lens system.

10. An instrument as recited in claim 9, wherein said plurality of interconnected lens tubes includes a third lens tube, said third lens tube having a cavity for receiving a proximal end of said second lens tube in overlapping engagement therewith.

11. An instrument as recited in claim 8, wherein said plurality of interconnected lens tubes includes a third lens tube, said third lens tube having a cavity for receiving a proximal end of said second lens tube in overlapping engagement therewith.

12. The instrument as recited in claim 1, including an aperture stop disposed between said first and second groups of optical elements.

13. The instrument as recited in claim 1, wherein said second group of optical elements includes a second lens, a third lens spaced proximally relative to said second lens, a fourth lens spaced proximally relative to said third lens, and a fifth lens spaced proximally relative to said fourth lens said fifth lens being a positive lens.

14. The instrument as recited in claim 13, wherein said fourth lens is a doublet containing a negative lens contiguous with a positive lens such that the aggregate sum of optical power of said fourth lens is negative.

15. The instrument as recited in claim 13, including an aperture stop disposed between said second and said third lenses.

16. The instrument as recited in claim 1, wherein said distal insertion portion includes an inner tip housing and an outer tip housing, each of said inner tip housing and said outer tip housing being coaxial with said optical axis wherein the interior of said outer tip housing and the exterior of said inner tip housing define a second annular space.

17. The instrument as recited in claim 16, including insufflation means for stimulating the tympanic membrane, said insufflation means including an insufflation path provided by said second annular space.

18. The instrument as recited in claim 1, including means for varying the linear distance between the first and second groups of optical elements along said optical axis.

19. The instrument as recited in claim 1, including insufflation means for stimulating the tympanic membrane through said insertion portion, said retrofocusing lens system being retained within said insertion portion so as not to interfere with the operation of said illumination means and said insufflation means.

20. An otological imaging instrument for viewing an ear interior, said instrument comprising:

an instrument housing including a frusto-conical insertion portion at a distal end thereof;

an electronic imager disposed in a proximal end of said instrument housing opposite said distal end;

illumination means disposed within said insertion portion for illuminating the interior of the ear for viewing; and a retrofocusing lens system for reducing an object onto said proximally disposed imager;

wherein said retrofocusing lens system includes a first group of optical elements positioned within the frusto-conical insertion portion of said instrument housing opposite from said proximal end and a second group of optical elements disposed proximally from said first group of elements and aligned therewith along an optical axis, said first group of optical elements including at least one negative lens and said second group of optical elements including a plurality of lenses having an aggregate positive optical power, whereby an optical image is imaged at a single imaging plane located at said proximally disposed imager using said retrofocusing lens system without the need of intermediate imaging planes wherein said distal insertion portion includes an inner tip housing and an outer tip housing, each of said inner tip housing and said outer tip housing being coaxial with said optical axis wherein the interior of said outer tip housing and the exterior of said inner tip housing define a second annular space, said instrument further including insufflation means for stimulating the tympanic membrane, said insufflation means including an insufflation path provided by said second annular space wherein said inner tip housing includes a plurality of circumferentially disposed flattened sections to provide vents for said insufflation means.

* * * * *